United States Patent [19]

Bouffard et al.

[11] 4,172,144

[45] Oct. 23, 1979

[54] SCHIFF'S BASE DERIVATIVES OF THIENAMYCIN

[75] Inventors: F. Aileen Bouffard, Scotch Plains; Burton G. Christensen, Metuchen; Nathan G. Steinberg, Plainfield, all of N.J.

[73] Assignee: Merck & Co., Inc., Rahway, N.J.

[21] Appl. No.: 907,643

[22] Filed: May 19, 1978

Related U.S. Application Data

[63] Continuation of Ser. No. 733,656, Oct. 18, 1976, abandoned, which is a continuation-in-part of Ser. No. 634,292, Nov. 21, 1975, abandoned.

[51] Int. Cl.$^2$ .................... A61K 31/40; C07D 487/04
[52] U.S. Cl. ................................ 424/274; 260/245.2; 260/326.12 R; 260/326.25; 424/250; 424/251; 424/263; 424/269; 424/270; 424/272; 424/273 R; 542/416; 544/239; 544/316; 544/355; 546/272; 548/336
[58] Field of Search .................. 260/326.31; 542/416; 424/274

[56] References Cited

U.S. PATENT DOCUMENTS 3,950,357  4/1976  Keehan et al. ................. 260/326.31

OTHER PUBLICATIONS

Derwent Abstract, 40279y (Nov. 19, 1976).

*Primary Examiner*—Donald G. Daus
*Assistant Examiner*—Mary C. Lee
*Attorney, Agent, or Firm*—Frank M. Mahon; James A. Arno; Julian S. Levitt

[57] ABSTRACT

Disclosed are Schiff's base derivatives of the antibiotic thienamycin, which has the following structure:

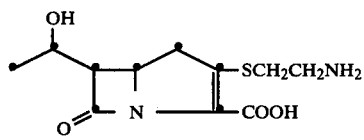

Such compounds and their pharmaceutically acceptable salt, ester and amide derivatives are useful as antibiotics. Also disclosed are processes for the preparation of such derivatives, pharmaceutical compositions comprising such derivatives, and methods of treatment comprising administering such derivatives and compositions when an antibiotic effect is indicated.

7 Claims, No Drawings

SCHIFF'S BASE DERIVATIVES OF THIENAMYCIN

BACKGROUND OF THE INVENTION

This is a continuation of U.S. patent application Ser. No. 733,656 filed Oct. 18, 1976, now abandoned which is a continuation-in-part of U.S. patent application 634,292 filed Nov. 21, 1975, now abandoned.

This invention relates to certain Schiff's base derivatives of the new antibiotic thienamycin. Such compounds and their pharmaceutically acceptable salt, ester and amide derivatives are useful as antibiotics. This invention also relates to processes for the preparation of such compounds, pharmaceutical compositions comprising such compounds and methods of treatment comprising administering such compounds and compositions when an antibiotic effect is indicated.

Thienamycin (I) is disclosed and claimed in co-pending commonly assigned U.S. patent application Ser. No. 526,992, filed Nov. 25, 1974 (now U.S. Pat. No. 3,950,357 issued Apr. 13, 1976), which patent is incorporated herein by reference since thienamycin may serve as, a starting material for the compounds of the present invention.

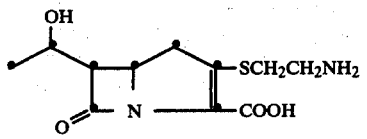

Other conveniently starting materials for the thienamycin derivatives of the present invention are shown below (Ia, Ib and Ic):

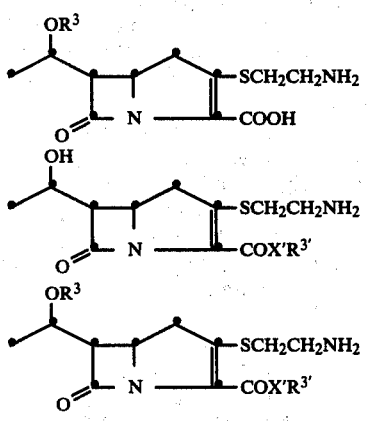

wherein $R^3$, $X'$ and $R^{3'}$ are defined below. Starting materials Ia, Ib and Ic, which are also useful as antibiotics, are disclosed and claimed in co-pending, concurrently filed U.S. patent applications Ser. No. 634,006, 634,298, and 634,294, respectively; all filed Nov. 21, 1975, and all now abandoned and their corresponding continuation-in-part U.S. patent applications Ser. Nos. 733,655; 733,651; and 733,652, respectively; all filed Oct. 18, 1976; and all now abandoned in favor to their corresponding continuation-in-part U.S. patent applications Ser. Nos. 861,234; 861,314; and 861,246, respectively; all filed Dec. 16, 1977. These applications are incorporated herein by reference as they describe useful starting materials and processes for converting species of the present invention to carboxyl-; O-; and carboxyl- and O-derivatized forms which are also embraced by the present invention and are useful as antibiotics.

The thienamycin derivatives of the present invention may be depicted by the following generic structural formula:

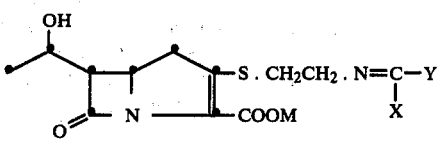

or, more conveniently, by the symbol:

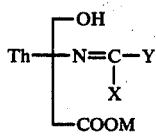

wherein:
"Th" symbolizes the bicyclic nucleus of theinamycin and the OH, amino and carboxyl groups of thienamycin are illustrated;

M is H, a salt cation selected from the alkali or alkaline earth metals or an amino salt; and X and Y are independently selected from the group consisting of hydrogen and $R^7$ wherein $R^7$ is substituted and unsubstituted alkyl, aryl, aralkyl, mono- and bicyclic heteroaryl and heteroaralkyl which typically comprise 4–10 ring atoms and the hetero atom or atoms are selected from O, S, or N. Such radicals X and Y, are established on the amino group of thienamycin through the methylene carbon by reacting thienamycin, or a derivative thereof, with an aldehyde or ketone of choice according to well-known procedures; X and Y and the aldehydes and ketones from which they are derived are defined more fully below. In the case where the Schiff's base is made from a cyclic ketone, such as 5,5-dimethyl-1,3-cyclohexanedione, the radicals X and Y are joined together.

The compounds of the present invention also embrace embodiments of the following structure:

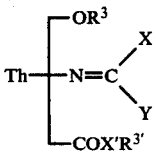

wherein the basic symbolism is as previously defined and $X'$ is oxygen, sulphur or NR' (R'=H or R); and $R^{3'}$ is inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of $R^{3'}$ is given in great detail below;

$R^3$ is 1. acyl (generically the group $OR^3$ is classifiable as an ester); or 2. $R^3$ is selected from alkyl, aryl, aralkyl and the like (such that the group $OR^3$ is generically classifiable as an ether). $R^3$ may also be hydrogen. The term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl-, and sulfenyl- radicals, and substituted P (III and V) radicals such as substituted phosphorous-, phosphoric-, phosphonous- and phosphinic- radicals, respectively. Such acyl radicals of the present invention are further defined below as are the radicals (2., above) which constitute the ether embodiments of the present invention.

Such O- and carboxyl derivatized embodiments, II, may be prepared by utilizing starting materials Ia, Ib and Ic (above), or they may be prepared from the corresponding thienamycin Schiff's base by procedures described below.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly, the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure of the antibiotic thienamycin but which are characterized as Schiff's base derivatives thereof. These antibiotics are active against a broad range of pathogens which representatively include both gram positive bacteria such as *S. aureus, S. pyogenes,* and *B. subtilis* and gram negative bacteria such as *E. coli, Proteus morganii* and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention are prepared according to well-known procedures for the preparation of Schiff's bases. The reaction may be illustrated by the following diagram:

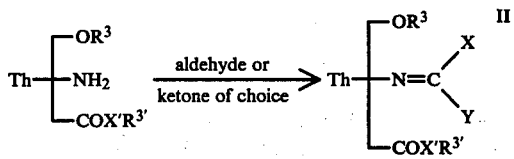

wherein all symbolism is as defined above. Suitable solvents include any inert solvent such as water, tetrahydrofuran (THF), dioxane, ether, lower alkanols such as methanol, ethanol and the like; or the reaction may be conducted without solvent in which case the aldehyde or ketone of choice serves as the solvent system. Typically, the reaction is conducted at from $-20°$ C. to $25°$ C. for from 15 minutes to 6 hours. It is to be noted that there are no undue criticalities of the reaction. The product is most conveniently isolated by evaporation of the solvent. Pharmaceutically acceptable salts of the compounds of the present invention are prepared by methods well known in the art (below).

Preferred compounds of the present invention are those wherein X and Y are independently selected from hydrogen and substituted or unsubstituted: alkyl having from 1 to 6 carbon atoms; alkenyl having from about 2 to 6 carbon atoms; alkynyl having from 2 to 6 carbon atoms; cycloalkyl having from 3 to 6 carbon atoms; cycloalkylalkyl having from 4 to 12 carbon atoms; aryl having from 6 to 10 carbon atoms; aralkyl having from 7 to 16 carbon atoms; mono- and bicyclic heteroaryl and heteroaralkyl having from 4 to 10 ring atoms one or more of which is a hetero atom selected from oxygen, sulphur or nitrogen wherein the alkyl moiety of the heteroaralkyl radical comprises 1 to 6 carbon atoms; mono- and bicyclic heterocyclyl and heterocyclylalkyl having from 4 to 10 ring atoms one or more of which is a hetero atom selected from oxygen, sulphur or nitrogen and wherein the alkyl moiety of the heterocyclylalkyl radical comprises from 1 to 6 carbon atoms; and wherein said substituent is selected from the group consisting of chloro, fluoro, bromo, iodo, mono-, di and trialkylamino wherein the alkyl moiety comprises from 1 to 6 carbon atoms; hydroxy, alkoxyl having from 1 to 6 carbon atoms, and alkylthio having from 1 to 6 carbon atoms. Representative examples of suitable aldehydes and ketones which provide such substituents, X and Y, are: salicylaldehyde, p-nitrobenzaldehyde, ethyl acetoacetate, acetylacetone, and the like; for cyclic ketones, such as 5,5-dimethyl-1,3-cyclohexanedione, X and Y are joined together to form a carbocyclic ring.

Identification of the Radical —COX′R$^{3'}$

In the generic representation of the compounds of the present invention (II, above), the radical represented by —COX′R$^{3'}$ is, inter alia, —COOH (X′ is oxygen and R$^{3'}$ is hydrogen) and all radicals known to be effective as pharmaceutically acceptable esters, anhydride (R$^{3'}$ is acyl) and amide radicals in the bicyclic β-lactam antibiotic art, such as the cephalosporins and penicillins and the nuclear analogues thereof.

Suitable radicals R$^{3'}$ include conventional protecting or carboxyl blocking groups. The term "blocking group" as utilized herein is employed in the same manner an in accordance with the teaching of U.S. Pat. No. 3,697,515, which is incorporated herein by reference. Pharmaceutically acceptable thienamycin derivatives of the present invention falling in this class are given below. Suitable blocking esters thus include those selected from the following list which is representative and not intended to be an exhaustive list of possible ester groups, wherein X=O and R$^{3'}$ is given:

(i) R$^{3'}$CR$^a$R$^b$R$^c$ wherein at least one of R$^a$, R$^c$ and R$^c$ is an electron-donor, e.g., p-methoxyphenyl, 2,4,6-trimethylphenyl, 9-anthryl, methoxy, CH$_2$SCH$_3$, tetrahydrofur-2-yl, tetrahydropyran-2-yl or fur-2-yl. The remaining R$^a$, R$^b$ and R$^c$ groups may be hydrogen or organic substituting groups. Suitable ester groups of this type include p-methoxybenzyloxycarbonyl and 2,4,6-trimethylbenzyloxycarbonyl.

(ii) R$^{3'}$ CR$^a$R$^b$R$^c$ wherein at least one of R$^a$, R$^b$ and R$^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R^{3'}CR^aR^bR^c$ wherein at least two of $R^a$, $R^b$ and $R^c$ are hydrocarbon such as alkyl, e.g., methyl or ethyl, or aryl, e.g., phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R^{3'}R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula: $R^4{}_3SiX'$; $R^4{}_2SiX'{}_2$; $R^4{}_3Si.NR^4{}_2$; $R^4{}_3Si.NH.COR^4$; $R^4{}_3Si.NH.CO.NH.SiR^4{}_3$; $R^4NH.CO.NH^4.SiR^4{}_3$; or $R^4C(OSiR^4{}_3)$; $HN(SiR^4{}_3)_2$ wherein $X'$ is a halogen such as chloro or bromo and the various groups $R^4$, which can be the same or different, represent hydrogen atoms or alkyl, e.g., methyl, ethyl, n-propyl, iso-propyl, aryl, e.g., phenyl, or aralkyl, e.g., benzyl groups.

More generally stated, pharmaceutically acceptable carboxyl derivatives of the present invention are those derived by reacting thienamycin or an N-protected form such as the Schiff's base or an N-acylated species (1, below) with alcohols, phenols, mercaptans, thiophenols, acylating reagents and the like; such products may then be derivatized to establish the $R^{3'}$ group of the compounds of the present invention (ii, above). For example, esters and amides of interest are the compounds of the formula II (above) having the following group at the 2-position: $-COX'R^{3'}$ wherein $X'$ is oxygen, sulfur, or $NR'$ ($R'$ is H or $R^{3'}$) and $R^{3'}$ is alkyl having 1-10 carbon atoms, straight or branched, such as methyl, ethyl, t-butyl, pentyl, decyl and the like; carbonylmethyl, including phenacyl, p-bromophenacyl, t-t-butylphenacyl, acetoxycetylmethyl, pivaloxyacetylmethyl, carboxymethyl, and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1-10 and preferably 1-6 carbon atoms; but can be branched, straight or cyclic, and the alkyl portion has 1-6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1-6 carbon atoms and the alkyl portion has 16 carbon atoms, such as acetoxymethyl, pivaloyloxymethyl, acetoxyethyl, propionyloxyethyl, acetoxypropyl and the like; haloalkyl wherein halo is chloro, bromo, fluoro or iodo, and the alkyl portion is straight or branched having 1-6 carbon atoms, e.g., 2,2,2-trichloroethyl, trifluoroethyl, 2-bromopropyl, diiodomethyl, 2-chloroethyl, 2-brmooethyl, and the like; alkenyl having 1-10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-yl-methyl, and the like alkynyl having 1-10 carbon atoms, either straight or branched e.g., 3-pentenyl, propargyl, ethynyl, 3-butyn-1-yl, and the like; alkanoyl, either straight or branched, having 1-10 carbon atoms, such as pivaloyl, acetyl, propionyl, and the like; aralkyl or heteroaralkyl wherein alkyl has 1-3 carbon atoms, and hetero means 1-4 atoms being selected from the group consisting of O, S, or N, such as benzyl, benzhydryl, and substituted benzyl, benzhydryl, or e.g., benzyl or benzhydryl substituted with 1-3 substituents such as benzyl, phenoxy, halo, loweralkyl, loweralkanoyloxy of 1-5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-courmaranmethyl, 5-indanylmethyl p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1-4 carbon atoms chain); or phthalidyl; or phenylethyl, 2-(p-methylphenyl)-ethyl, and the arylthioalkyl analogues, aryloxyalkyl wherein aryl is preferably a phenyl ring having 0-3 substituents preferably 0 or 1 substituents in the ortho or para positions and alkyl is 1-6 carbon atoms, e.g., (4-methoxy)-phenoxymethyl, phenoxymethyl, (4-chloro)phenoxymethyl, (4-nitro)phenoxymethyl, (4-benzyloxy)phenoxymethyl, (4-methyl)-phenoxymethyl, (4-benzyloxy)phenoxymethyl, (4-methyl)phenoxymethyl, (2-methoxy)phenoxymethyl, (1-phenoxy)ethyl, (4-amino)phenoxymethyl, (4-methoxy)phenylthiomethyl (4-chloro)phenylthiomethyl, phenylthioethyl; aryl wherein aryl is phenyl, 5-indanyl, or substituted phenyl having 0-3 substituents, preferably 0 or 1 substituent in the ortho or para position, e.g., (4-methyl)phenyl, (4-hydroxy)-phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)-benzyloxymethyl, (4-chloro)benzyloxymethyl; alkylthioalkyl wherein the alkylthio portion has 1-10 and preferably 1-6 carbon atoms, but can be branched, straight or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein $X'$ is the

group. Representative of such amides are those wherein $R'$ is selected from the group consisting of hydrogen, methyl, ethyl, phenyl, p-methoxyphenyl, benzyl, carboxymethyl, methylthioethyl, and heteroaryl; also embraced by $-COX'R^{3'}$ are anhydrides wherein $R^{3'}$ is benzyloxycarbonyl, ethoxycarbonyl, benzoyl, and pivaloyl.

Particularly preferred esters are those wherein X' is oxygen and R³' is aralkyl, aryloxyalkyl, and aralkoxyalkyl, alkylthioalkyl, haloalkyl and alkenyl.

The most preferred —COX'R³' radicals of the present invention are those wherein (relative to Structure II above) X' is oxygen, sulphur or NR' (R' is selected from the group consisting of hydrogen and lower alkyl); and R³' is selected from the group consisting of: lower alkyl, lower alkenyl such as methallyl, 3-methylbutenyl, 3-butenyl, and the like; methylthioethyl; benzyl and substituted benzyl, such as p-t-butylbenzyl, m-phenoxybenzyl, p-pivaloyloxybenzyl, p-nitrobenzyl and the like; pivaloyloxymethyl, 3-phthalidyl, acetoxymethyl, propionyloxymethyl, acetylthiomethyl, pivaloylthiomethyl, allyl, 3-butenyl, 4-pentenyl, 2-butenyl, 3-methyl-2-butenyl, phenacyl, acetoxyacetylmethyl, pivaloylacetylmethyl, diethylaminoethyl, dimethylaminoethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl acetamidomethyl.

Identification of R³

In the generic representation of the present invention, Structure ii (above), the radical R³ is, in addition to hydrogen, 1. acyl (generically the term —OR³ is classifiable as an ester); or 2. R³ is selected from alkyl, aryl, aralkyl, and the like such that the group —OR³ is classifiable as an ether. For the ester embodiments 1. R³ is selected from the following definition of acyl radicals. In the so-called ether embodiments 2. of the present invention, R³ is selected from the same acyl radicals wherein the carbonyl moiety,

or more generally

is deleted; thus R³ is selected from the following radicals wherein p is 0 or 1 and all other symbolism is defined below:

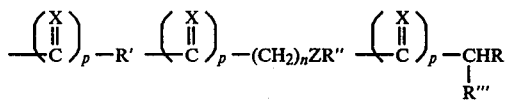

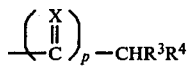

Thus, relative to the definition of R³, the acyl radical can, inter alia, be substituted or unsubstituted aliphatic, aromatic or heterocyclic, araliphatic or heterocyclylaliphatic carboxylic acid radical, a substituted or unsubstituted carbamyl radical or a carbothioic acid radical.

One group of acyl radicals can be represented by the general formula:

wherein X is O or S and R" represents hydrogen; substituted amino such as dialkylamino wherein the alkyl radical comprises 1 to about 6 carbon atoms; substituted or unsubstituted: straight or branched chain alkyl wherein the alkyl radical comprises 1 to about 6 carbon atoms; mercapto such as alkylthio, typically comprising 1 to 6 carbon atoms; arylthio, typically comprising 6 to 10 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4–10 atoms and the hetero atom or atoms are selected from O, N and S; such above-listed groups can be unsubstituted or can be substituted by radicals such as OH, SH, SR (R is lower-alky or aryl such as phenyl), alkyl or alkoxy groups having 1 to about 6 carbon atoms, halo, such as Cl, Br, R and I, cyano, carboxy, sulfamino, carbamoyl, sulfonyl, azido, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-N-benzoylamino-4-carboxy-n-butyl, p-dimethylaminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-iosxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2- and 3-thienylaminomethyl, 2-(5-nitrofuranyl)vinyl, phenyl, o-methoxyphenyl, o-chlorophenyl, o-phenylphenyl, 1-(5-cyanotrizolyl)-methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(methoxythienyl)methyl, 2- or 3-(4-chlorothienyl)- methyl, 2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl) methyl, 2-furylmethyl, 2-(5-nitrofuryl)methyl, 3-furylmethyl, 2-theinylmethyl, 3-thienylmethyl, tetrazolylmethyl benzamidinomethyl and cyclohexylamidinomethyl.

The acyl group can also be a radical of the formula:

wherein X is O or S and n is 0–4, Z represents oxygen, sulfur, carbonyl or nitrogen and R" is defined as above. Representative members of the substituent

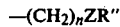

that might be mentioned are allylthiomethyl, phenylthiomethyl, butylmercaptomethyl, α-chloroacrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, methylamino, dimethylamino, pyridinium methyl, trimethylammonium-methyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

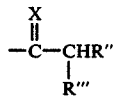

wherein R" is defined as above and R'" is a radical such as hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent

that might be mentioned are α-(methylamino)benzyl, D(−)-α-hydroxybenzyl, α-carboxybenzyl, α-(5-tetrazolyl)-benzyl, 2-thienyl-carboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(−)-2-thienyl-guanidinomethyl, D(−)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)aminomethyl, 2-(5-chlorothienyl)-hydroxymethyl, 2-(5-chlorothienyl)-carboxymethyl, 3-(1,2-thiazolyl)-aminomethyl 3-(1,2-thiazolyl)-hydroxymethyl, 3-(1,2-thiazolyl)carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are those wherein R" represents hydrogen, halo, such as chloro, fluoro, bromo, iodo, guanidino, phosphono, hydroxy, tetrazolyl, carboxy, sulfo, or sulfamino and R'" represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl of 1–6 carbon atoms, heterocyclic or substituted heterocyclic thio groups; or cyano. The substituents on the moieties, $R^{3''}$ and R" can be halo, carboxymethyl, guanidino, guanidinomethyl, carboxamidomethyl, aminoethyl, nitro, methoxy or methyl. When R" is selected from the group consisting of hydrogen, hydroxy, or carboxy and R'" is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, αguanidiono-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl radical may also be selected from sulphur (1) and phosphorus (2) radicals:

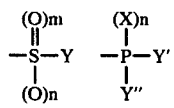

wherein with respect to (1), m and n are integers selected from 0 or 1 and Y=O$^\ominus$ M$^\oplus$, —N(R")$_2$, and R"; wherein M$^\oplus$ is selected from hydrogen alkali metal cations and organic bases; and R" is as defined above, e.g., alkyl, alkenyl, aryl and heteroaryl. With respect to (2) X=0 or S; n=0 or 1; and Y' and Y" are selected from the group consisting of O$^\oplus$M$^\ominus$, —N(R")$_2$, R" and ZR" wherein all symbolism is as defined above, e.g., R" and ZR" are representatively: alkyl, alkenyl, aryl, heteroaryloxy; Y' and Y'", including R" moieties, can be joined together to form cyclic ester, ester- amide and amide functions. Illustrative examples of (1) are O-(methylsulphonyl)thienamycin, O-(o-nitrophenylsulphonyl)-thienamycin, O-(p-chlorophenylsulphinyl)-thienamycin, O-(o-nitrophenylsulphenyl)thienamycin, O-(sulphamoyl)thienamycin, O-(dimethylsulphamoyl)-thienamycin, and thienamycin O-(sulphonic acid sodium salt). Illustrative examples of (2) are O-(dimethoxyphosphino)thienamycin, O-(dibenzyloxyphosphino)-thienamycin, O-(dihydroxyphosphino)thienamycin, O-(dimethoxyphosphinothioyl)thienamycin, O-(dibenzyloxyphosphinyl)thienamycin, and O-(dihydroxyphosphinyl)thienamycin.

An acyl class of particular interest is those acyl radicals which are selected from the group consisting of conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkylsilyl, for example, trimethylsilyl and t-butyldimethylsilyl are also of interest.

The following radicals, according to the foregoing definition of acyl are preferred:

formyl, propionyl, butyryl, chloroacetyl, methoxyacetyl, methoxycarbonyl, ethoxycarbonyl, methylcarbamoyl, ethylcarbamoyl, phenylthiocarbonyl, N-methylaminoacetyl, N,N-dimethylaminoacetyl, N,N,N-trimethylaminoacetyl, 3-(N,N-dimethyl)aminopropionyl, 3-(N,N,N-trimethyl)amino propionyl, N,N,N-triethylaminoacetyl, pyridiniumacetyl, quanylthioacetyl, guanidinoacetyl, 3-guanidinopropionyl, $N^3$-methyl-guanidinopropionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfo, phosphono, sulfoacetylaminoacetyl, phosphonoacetylaminoacetyl, $N^3$-dimethylaminoacetamidinopropionyl, ureidocarbonyl, dimethylaminoguanylthioacetyl, 3-(1-methyl-4-pyridinium)propionyl, 3-(5-aminoimidazol-1-yl)propionyl, 3-methyl-1-imidazoliumacetyl, 3-sydnonylacetyl, $$-\overset{O}{\underset{\|}{P}}(OCH_3)_2, \quad -\overset{S}{\underset{\|}{P}}(OCH_3)_2, \quad -\overset{S}{\underset{\|}{P}}\overset{OCH_3}{\underset{ONa}{\diagdown}}, \quad -\overset{S}{\underset{\|}{P}}[N(CH_3)_2]_2,$$

$$-\overset{O}{\underset{\|}{P}}\overset{N(CH_3)_2}{\underset{ONa}{\diagdown}}, \quad -\overset{O}{\underset{\|}{P}}[N(CH_3)_2]_2, \quad -\overset{S}{\underset{\|}{P}}\overset{N(CH_3)_2}{\underset{ONa}{\diagdown}}$$

However, it is to be understood that any acyl radical may be employed in the practice of the invention and is to be considered within the scope of the invention.

Preparation of Starting Materials Ia, Ib and Ic

The above-described starting materials are conveniently prepared from an N-protected thienamycin such as an N-acylated thienamycin (1).

$$Th \begin{cases} -OH \\ -NR^1R^2 \\ -COOH \end{cases} \quad \underline{1}$$

wherein $R^1$ and $R^2$ are selected from hydrogen and the above-defined acyl radicals. Preferably $R^1$ is hydrogen and $R^2$ is an easily removable blocking group such as: carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkylsilyl, for example, trimethylsilyl, and t-butyldimethylsilyl are also of interest. The most preferred N-blocking groups are substituted and unsubstituted carbobenzyloxy radicals:

$$R^2 = -\overset{O}{\underset{\|}{C}}-OCH_2-\underset{(R')_n}{\underset{\diagdown}{\diagdown}}$$

wherein n is 0–2 (n=0, R'=hydrogen) and R' is lower alkoxy or nitro; and bromo-t-butoxycarbonyl.

The ultimate N-deblocking procedure for the preparation of Ia, Ib or Ic is accomplished by any of a variety of well-known procedures which include hydrolysis or hydrogenation; when hydrogenation is employed suitable conditions involve a solvent such as a loweralkanoyl in the presence of a hydrogenation catalyst such as palladium, platinum or oxides thereof.

The N-acylated intermediate (1, above) is prepared by treating thienamycin (I) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic-carbonic anhydrides; also, carboxylic acids in the presence of a carbodiimide such as 1,3-dicyclohexylcarbodiimide, and an activated ester of a carboxylic acid such as the p-nitrophenyl ester.

Such N-acylated thienamycin starting materials are fully described in co-pending, concurrently filed U.S. patent application Ser. No. 634,291 filed Nov. 21, 1975 and in its continuation-in-part U.S. patent application Ser. No. 733,653, filed Oct. 18, 1976, and now abandoned in favor of its continuation-in-part U.S. patent application Ser. No. 861,247, filed Dec. 16, 1977. These applications are incorporated herein by reference.

The acylation reaction may be conducted at a temperature in the range of from about −20° to about 100° C., but is preferably conducted at a temperature in the range of from −9° to 25° C. Any solvent in which the reactants are soluble and substantially inert may be employed, for example polar solvents such as water, alcohols and polar organic solvents in general such as dimethylformamide (DMF), hexamethylphosphoramide (HMPA), acetone, dioxane tetrahydrofuran (THF), acetonitrile, heterocyclic amines such as pyridine, ethylacetate, aqueous mixtures of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

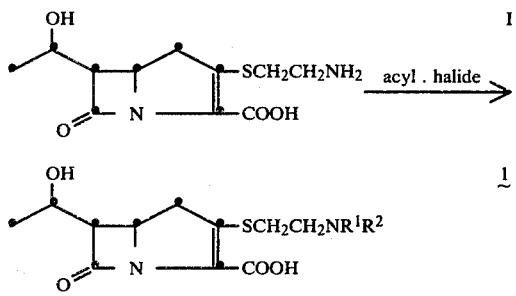

Generally when the above-described acylating reaction employs an acid halide (suitable halides are chloro, iodo, or bromo) or anhydride the reaction is conducted in water or an aqueous mixture of a polar organic solvent such as acetone, dioxane, THF, DMF, acetonitrile or the like in the presence of a suitable acceptor base such as $NaHCO_3$, $MgO$, $NaOH$, $K_2HPO_4$ and the like.

In carrying out the reactions described herein, it is generally not necessary to protect the 2-carboxy group or the 1'-hydroxy group; however, in cases where the acylating reagent is exceedingly water sensitive it is sometimes advantageous to perform the acylation in a non aqueous solvent system. Triorganosilyl (or tin) derivatives of thienamycin proceed rapidly to give the tris-triorganosilyl derivative, for example tris-trimethylsilyl Thienamycin $TH(TMS)_3$:

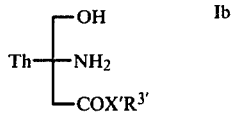

Such derivatives, which are readily soluble in organic solvents, are conveniently prepared by treating thienamycin with an excess of hexamethyldisilizane and a stoichiometric amount of trimethylchlorosilane at 25° C., with vigorous stirring under a $N_2$ atmosphere. The resulting $NH_4Cl$ is removed by centrifugation and the solvent is removed by evaporation to provide the desired silyl derivative.

The intermediate starting materials Ib are prepared according to the following scheme:

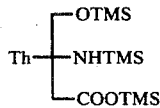

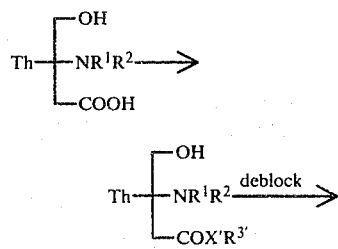

wherein all symbolism is as previously defined.

In general, the transformation (1→Ib) is accomplished by conventional procedures known in the art. Such procedures include:

1. Reaction of 1 with a diazoalkane such as diazomethane, phenyldiazomethane, diphenyldiazomethane, and the like, in a solvent such as dioxane, ethylacetate, acetonitrile and the like at a temperature of from 0° C. to reflux for from a few minutes to 2 hours.

2. Reaction of an alkali metal salt of 1 with an activated alkyl halide such as methyl iodide, benzyl bromide, or m-phenoxybenzyl bromide, p-t-butylbenzyl bromide, pivaloyloxymethyl chloride, and the like. Suitable reaction conditions include solvents such as hexamethylphosphoramide and the like at a temperature of from 0° C. to 60° C. for from a few minutes to 4 hours.

3. Reaction of 1 with an alcohol such as methanol, ethanol, benzyl alcohol, and the like. This reaction may be conducted in the presence of a carbodiimide condensing agent such as dicyclohexylcarbodiimide or the like. Suitable solvent, at a temperature of from 0° C. to reflux for from 15 minutes to 18 hours, include $CHCl_3$, $CH_3CH$, $CH_2Cl_2$ and the like.

4. Reaction of an N-acylated acid anhydride of 1 prepared by reacting the free acid 1 with an acid chloride such as ethylchloroformate, benzychloroformate and the like, with an alcohol such as those listed in 3. under the same conditions of reaction as given above for 3. The anhydride is prepared by reacting 1 and the acid chloride in a solvent such as tetrahydrofuran (THF), $CH_2Cl_2$ and the like at a temperature of from 25° C., to reflux for from 15 minutes to 10 hours.

5. Reaction of labile esters of thienamycin such as the trimethylsilyl ester, dimethyl-t-butylsilyl ester or the like with $R^{3'}X$ wherein X is halogen such as bromo and chloro and R is as defined, in a solvent such as THF, $CH_2Cl_2$ and the like at a temperature of from 0° C. to reflux for from 15 minutes to 16 hours. For example according to the following scheme:

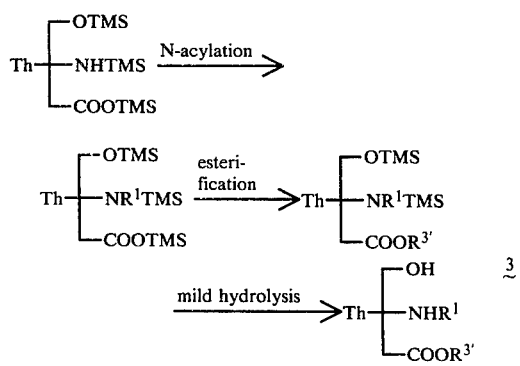

wherein TMS is triorganosilyl such as trimethylsilyl and all other symbolism is as previously defined.

The amides of the present invention are most conveniently prepared by reacting the acid anhydride of Ib (X=O, R=acyl) with ammonia or with the amine of choice, e.g., the alkyl-, dialkyl-, aralkyl- or hetero cyclic amines listed above.

The above-recited schemes of esterification are well-known in the related bicyclic β-lactam antibiotic art and indeed in all of general organic synthesis and it is to be noted that there is no undue criticality of reaction parameters in the preparation of the carboxyl derivatives Ib useful as starting materials in the practice of the present invention. Further, it should be noted that direct esterification (I→Ib) is also possible without providing for N-protection.

Starting materials Ia and Ic are conveniently prepared by any of a variety of well-known esterification of etherification reactions upon the secondary alcoholic group of Ib. Such procedures include:

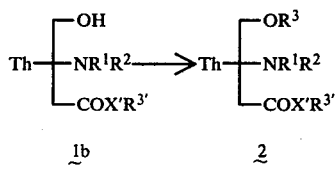

1. For the preparation of ether embodiments of the present invention, the acid catalized reaction of 1b with a diazoalkane such as diazomethane, phenyldiazomethane, diphenyldiazomethane and the like in an inert solvent such as dioxane, tetrahydrofuran (THF), halohydrocarbons such as $CH_2Cl_2$, ethylacetate and the like in the presence of a catalytic amount of a strong acid or Lewis acid such as toluenesulfonic acid, trifluoroacetic acid, fluoboric acid, Boron trifluoride and the like at a temperature of from $-78°$ C. to $25°$ C. for from a few minutes to 2 hours.

2. For the preparation of ether embodiments of the present invention, the reaction of 1b with an alkylating agent such as active halides, for example, methyliodide, benzylbromide, m-phenoxybenzylbromide and the like and alkyl sulphonates such as dimethylsulphate, diethylsulphate, methylfluorosulphonate and the like in the presence of a strong base capable of forming the alcoholate anion of 1b. Suitable bases include alkali and alkaline earth metal oxides and hydrous oxides, alkali metal alkoxides such as potassium tertiary butoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from $-78°$ C. to $25°$ C., for from a few minutes to 4 hours.

3. For the preparation of ester embodiments, of the present invention, the reaction of 1b with any of the above-listed acyl radicals in their acid form. The reaction may be conducted in the presence of a carbodiimide condensing agent such as dicyclohexylcarbodiimide or the like. Suitable solvents include any inert solvent such as $CHCl_3$, $CH_2Cl_2$, DMF, HMPA, acetone, dioxane and the like at a temperature of from $0°$ C. to $60°$ C., for from 15 minutes to 12 hours.

4. For the preparation of ester embodiments of the present invention, the reaction of 1b with an acyl halide or an acid anhydride, wherein the acyl moiety is described above. Generally, when the above-described acylating reaction employs an acid halide (suitable halides are chloro, iodo, or bromo or acid anhydride) the reaction is conducted in an anhydrous organic such as acetone, dioxane, methylenechloride chloroform, DMF, or the like in the presence of a suitable acceptor base such as $NaHCO_3$, MgO, triethylene, pyridine, and the like at a temperature of from $0°$ C. to $40°$ C., for from 1 to 4 hours.

Suitable acyl halides and anhydrides include: acetic anhydride, bromoacetic anhydride, propionic anhydride, benzoylchloride, phenylacetyl, chloride azidoacetyl chloride, 2-thienylacetyl chloride, 2-, 3- and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl, ethyl carbonic anhydride, methylchloroformate, bis(p-nitrobenzyl)phosphorochloridate and the like.

5. For the preparation of ester embodiments of the present invention, the reaction of 1b with a suitably substituted ketene or isocyanate such as ketene, dimethyl ketene, methylisocyanate, methylisothiocyanate, chlorosulfonyl isocyanate and the like. Suitable solvents include dioxane, tetrahydrofuran, chloroform and the like at a temperature of from $-70°$ C. to $60°$ C., for from 15 minutes to 18 hours.

The intermediate 2 is then N-deblocked as described above to provide starting material Ic. From Ic, Ia is prepared by deblocking the carboxyl group:

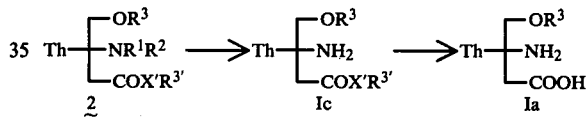

Starting material Ia is conveniently and preferably obtained when X' is oxygen and R$^{3'}$ is a readily removable carboxyl protecting or blocking group (see above). Starting material Ia is prepared by deblocking according to any of a variety of well-known procedures which include hydrolysis and hydrogenation. When the preferred carboxyl-blocking groups are employed (below), the preferred deblocking procedure is hydrogenation; wherein the intermediate species (Ic or 2) in a solvent such as a lower alkanoyl, is hydrogenated in the presence of a hydrogenation catalyst such as palladium, platinum or oxides thereof.

In this connection, it is noted that suitable "blocking groups" R$^{3'}$ include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1–10 carbon atoms. For example, suitable "blocking groups" R$^{3'}$ include benzyl, phenacyl, p-nitrobenzyl, methoxymethyl, trichloroethyl, trimethylsilyl, tributyltin, p-methoxybenzyl, benzhydryl. These blocking groups are preferred since they are generally recognized easily-removable blocking groups in cephalosporin and penicillin art.

The preferred carboxyl blocking groups, are benzyl and substituted benzyl:

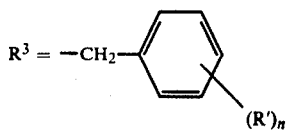

wherein n, n=0–2(n=0, R'=H) and R' is loweralkoxyl or nitro.

In the alternative it should be noted that the compounds of the present invention may be arrived at by operating upon the Schiff's base of thienamycin to achieve derivatization by establishment of $R^3$ and/or —$COX'R^{3'}$. Such procedures are exactly as described above except that the Schiff's base species replaces the N-acylated species and, of course, there is no need to N-deblock.

The products of this invention (II) form a wide variety of pharmacologically acceptable salts with inorganic and organic bases; these include, for example, metal salts derived from alkali or alkaline earth metal hydroxide, carbonates or bicarbonates and salts derived from primary, secondary or tertiary amines such as monoalkylamines, dialkylamines, trialkylamines, lower alkanolamines, di-lower alkanolamines, lower alkylenediamines, N,N-diaralkyl lower alkenediamines, aralkylamines, amino substituted lower alkanols, N,N-di-lower alkylamino substituted lower alkanols, amino-, polyamino- and guanidino-substituted lower alkanoic acids and nitrogen-containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Acid addition salts, e.g., with hydrochloric hydrobromic, sulfuric nitric, toluene-p-sulphonic and methane sulphonic acids may also be employed, in such instances where the acyl radical contains a basic group.

The salts can be mono-salts such as the monosodium salt obtained by treating one equivalent of sodium hydroxide with one equivalent of the product (II), also mixed di-salts. Such salts may be obtained by treating one equivalent of a base having a divalent cation, such as calcium hydroxide, with one equivalent of the product (II). The salts of this invention are pharmacologically acceptable nontoxic derivatives which can be used as the active ingredient in suitable unit-dosage pharmaceutical forms. Also, they may be combined with other drugs to provide compositions having a broad spectrum of activity.

The novel Thienamycin derivatives of the present invention are valuable antimicrobial substances which are active against various gram-positive and gram-negative pathogens such as *Bacillus subtilis, Salmonella schottmuelleri* and *Proteus vulgaris*. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria, and accordingly, find utility in human and veterinary medicine. The compounds of this invention can therefore be used as antibacterial drugs for treating infections caused by gram-positive or gram-negative bacteria, for example, against *Staphylococcus aureus, Escherichia coli, Klebsiella pneumoniae, Bacillus subtilis, Salmonella typhosa, Pseudomonas* and *Bacterium proteus*. The antibacterials of the invention may further be utilized as additives to animal feedingstuffs, for preserving foodstuffs and disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions of elixirs. They may be administered orally intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc., or may be presented as a dry product, for reconstitution with water or other suitable vehicles before use. Such liquid preparations may contain conventional additives such as suspending agents, for example, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional bases, e.g., cocoa butter or other glyceride.

Compositions for injection may be presented in unit dose form in ampules, or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparation may be presented in individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be adminstered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms, as for example, in solid or liquid orally ingestible dosage form. The compositions per unit dosage, whether liquid or solid may contain from 0.1% to 99% of active material, the preferred range being from about 10-60%. The compositions will generally contain from about 15 mg. to about 1500 mg. of the active ingredient; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution.

The following Examples, illustrate but do not limit the product, process, compositional or method of treatment aspects of the present invention.

EXAMPLE 1

Preparation of Methyl Acetonacetate Schiff Base Derivative of Thienamycin

To a suspension of 10.6 mg. of Thienamycin in 2 ml. of methanol at 0° C. is added, under $N_2$, 73 μl. of 0.5N potassium hydroxide in alcohol; methyl acetoacetate (4.6 μl.) is added and the reaction is allowed to stand for ½ hour at 0° C. U.V. analysis shows 65% of the initial absorbance at λ 290 nm remains. The material is placed on 20 ml. of XAD resin and the product is eluated with deionized water, followed with tetrahydrofuran:water (10:90). The fractions containing the product are combined and freeze-dried (1.9 mg.). Electrophoresis shows a bioactive spot having a mobility towards the positive pole. This spot shows antibacterial activity against *S. aureus*.

EXAMPLE 2

Preparation of Acetylacetone Schiff Base Derivative of Thienamycin

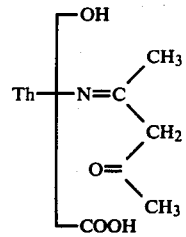

Thienamycin (10 mg.) is suspended in 2.0 ml. of acetyl acetone. The suspension is stirred at 0° C. under $N_2$, and then at 25° C. for 6 hours. The reaction mixture is extracted with ether, and the ether is evaporated. The residue shows bioactivity upon bioautography vs. *S. aureus* after electrophoresis.

EXAMPLE 3

Preparation of 2-Hydroxy-naphthaldehyde Schiff Base of Thienamycin

Thienamycin (15 mg.) is dissolved in 1.6 ml. of dry tetrahydrofuran. To this clear solution is added 111 μl. of hexamethyldisilazane and 20 μl. of trimethylsilane. The reaction mixture is stirred for ½ hour at 25° C. and is evaporated to dryness in vacuo. To the residue is added 1 ml. of dry tetrahydrofuran, followed by the addition of 3.1 mg. of 2-hydroxynaphthaldehyde. The reaction mixture is stirred for 2 hours, at 25° C.

The reaction is cooled, and brought to pH 4 with phosphoric acid buffer. The reaction is allowed to progress for two minutes at which time the pH is adjusted to 6.8 with $5 \times 10^{-2}$ sodium hydroxide solution. The organic solvent is removed in vacuum at 25° C. during which the pH remained at 6.8. The solution is filtered and freeze dried. Electrophoresis (504 c.m., pH 7 phosphate buffer) followed by bioautography against *S. aureus* shows a bioactive zone which moves toward the anode.

EXAMPLE 4

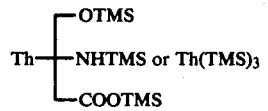

TMS = trimethylsilyl

Preparation of Silylated-Thienamycin

Thienamycin (80.0 mg.) is suspended in 40 ml. tetrahydrofuran (THF) and under a $N_2$ atmosphere and is concentrated to 10 ml.; hexamethyldisilazane (1.0 ml.) and trimethylchlorosilane (300 μl.) is added. The mixture is reacted for 20 mins. at 25° C. with vigorous stirring. The suspension is then centrifuged to remove ammonium chloride. The supernatant is evaporated to an oil under a nitrogen stream for future reaction.

EXAMPLE 5

N-Salicylidene Thienamycin Benzyl Ester

Thienamycin (115 mg) is dissolved in 4 ml. of 50% aqueous dioxane. The solution is cooled to 0° C. and titrated to pH 5 with N sulfuric acid. Phenyldiazomethane 60 mg in 0.9 ml. of dioxane is added during 5 minutes with vigorous stirring while the pH is maintained at 5-5.5 under control of a pH state. After reacting an additional 5 minutes the mixture is extracted with ether. The aqueous layer is adjusted to pH 8.3 with sodium bicarbonate solution and extracted with ethyl acetate. To the solution containing thienamycin benzyl ester is added 35 µl. of salicyladehyde and anhydrous magnesium sulfate. The solution is concentrated to 1 ml. on the rotary evaporator and allowed to stand at 25° C. for one hour. The course of the reaction is followed by TLC on silica gel in 20% methanol-chloroform. A new spot at Rf 0.8 appears. The product is isolated by preparative TLC in 50% ethylacetate-chloroform and appears as a yellow band at Rf 0.32; U.V. $\lambda_{max}$ 259 mµ and 322 mµ of equal intensity. d(CH$_3$CHOH); 6.7-7 and 5.7-6.4 (multiplex); 4.72, s,(OC$\underline{H}_2$); 2.5-7.5 (multiplex aromatic H) and 1.75, s,

Following the above procedure but substituting diphenyl diazomethane for phenyldiazomethane there is obtained salicylidene thienamycin benzhydryl ester NMR 8.67

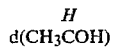

5.65-7.1 (aliphatic multiplex); 2.5-3.2 (aromatic multiplex) 1.67

Following the above procedure but substituting p-nitro benzaldehyde for salicyaldehyde there is obtained p-nitrobenzylidene thienamycin benzyl ester and the corresponding benzhydryl ester. TLC 5:1 CHCl$_3$ EtOH Rf 0.8. Similarly, when benzaldehyde, p-bromobenzaldehyde, p-dimethylaminobenzaldehyde, 5,5-dimethyl-1,3-cyclohexanedione, dimethylaminoacetaldehyde, and isobutyraldehyde are substituted for salicyaldehyde the corresponding benzhydryl and benzyl ester are obtained.

EXAMPLE 6

Preparation of Pharmaceutical Compositions

One such unit dosage form consists in mixing 120 mg. of acetylacetone Schiff base derivative of thienamycin with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| Acetylacetone Schiff Base derivative of Thienamycin | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| | PER TABLET |
|---|---|
| FARENTERAL SOLUTION | |
| Ampoule: | |
| Acetylacetone Schiff base derivative of Thienamycin | 500 mg. |
| Diluent: Sterile Water for Injection | 2 cc. |
| OPTHALMIC SOLUTION | |
| Acetylacetone Schiff base derivative of Thienamycin | 100 mg. |
| Hydroxypropylmethyl Cellulose | 5 mg. |
| Sterile Water | to 1 ml. |
| OTIC SOLUTION | |
| Acetylacetone Schiff base derivative of Thienamycin | 100 mg. |
| Benzalkonium Chloride | 0.1 mg. |
| Sterile Water | to 1 ml. |
| TOPICAL OINTMENT | |
| Acetylacetone Schiff base derivative of Thienamycin | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

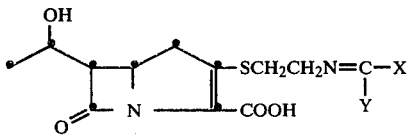

and the pharmaceutically acceptable salts thereof; wherein X and Y are independently selected from hydrogen; alkyl having from 1 to 6 carbon atoms; alkenyl having from 2 to 10 carbon atoms; alkynyl having from 2 to 6 carbon atoms; cycloalkyl having from 3 to 6 carbon atoms; cycloalkylalkyl- having from 4 to 12 carbon atoms; aryl having from 6 to 10 carbon atoms; and aralkyl having from 7 to 16 carbon atoms.

2. A compound having the structural formula:

3. A compound having the structural formula:
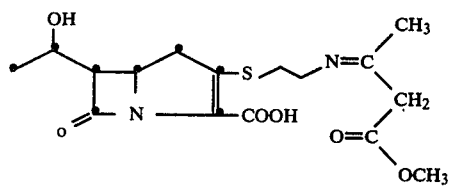
4. A compound having the structural formula:
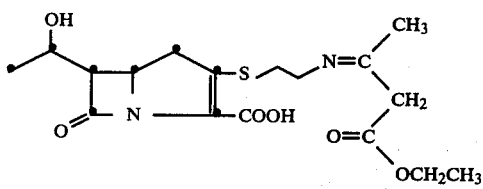
5. A compound having the structural formula:
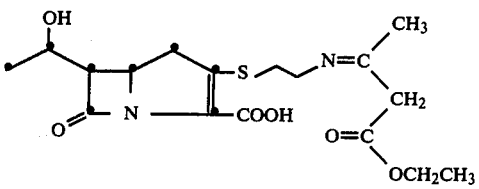
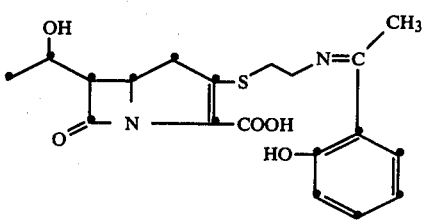
6. A compound having the structural formula:
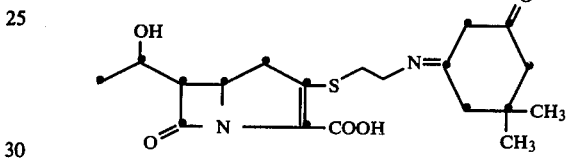
7. An antibiotic pharmaceutical composition comprising, in unitary dosage form, a therapeutically effective amount of a compound according to claim 1 and a pharmaceutical carrier therefor.
* * * * *